United States Patent [19]

Matier et al.

[11] Patent Number: 4,508,725
[45] Date of Patent: Apr. 2, 1985

[54] ESTERS OF 3-(3-SUBSTITUTED-AMINO-2-HYDROXY-PROPOXY)-4-SUBSTITUTED-1,2,5-THIADIAZOLE DERIVATIVES

[75] Inventors: William L. Matier, Libertyville; Paul W. Erhardt, Mundelein; Ghanshyam Patil, Vernon Hills, all of Ill.

[73] Assignee: American Hospital Supply Corporation, Evanston, Ill.

[21] Appl. No.: 452,280

[22] Filed: Dec. 22, 1982

[51] Int. Cl.³ .................. C07D 285/10; A61K 31/41
[52] U.S. Cl. ..................................... 514/362; 548/135
[58] Field of Search ......................... 548/135; 424/269

[56] References Cited

U.S. PATENT DOCUMENTS

| | | | |
|---|---|---|---|
| 3,655,663 | 4/1972 | Wasson | 548/135 |
| 3,729,469 | 4/1973 | Wasson | 548/135 |
| 3,729,477 | 4/1973 | Wasson | 548/135 |
| 3,891,639 | 6/1975 | Wasson | 544/134 |
| 4,011,217 | 3/1977 | Wasson | 544/134 |
| 4,051,144 | 9/1977 | Weinstock et al. | 548/135 |
| 4,076,939 | 2/1978 | Belanger | 548/135 |
| 4,127,674 | 11/1978 | Leopold | 424/324 |

*Primary Examiner*—Robert Gerstl
*Attorney, Agent, or Firm*—Donald L. Barbeau; Gildo E. Fato

[57] ABSTRACT

Novel compounds are disclosed having the formula

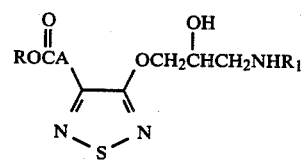

wherein R is lower alkyl, lower cycloalkyl, lower haloalkyl, lower alkylcarboxymethyl, arylcarboxymethyl, lower alkenyl, lower alkynyl, aryl having from 6 to about 10 carbon atoms, or aralkyl; $R_1$ is lower alkyl, lower hydroxyalkyl, lower alkenyl, lower alkynyl, aralkyl, or —WB; where W is alkylene containing from 1 to about 10 carbon atoms; and B is —$NR_2COR_3$, —$NR_2CONR_3R_4$, —$NR_2SO_2R_3$, —$NR_2SO_2NR_3R_4$, or —$NR_2COOR_5$, where $R_2$, $R_3$, $R_4$, and $R_5$ may be the same or different and may be hydrogen, alkyl, alkoxyalkyl, alkoxyaryl, cycloalkyl, alkenyl, alkynyl, aryl, heteroaryl, or aralkyl, except that $R_3$ and $R_5$ are not hydrogen when B is —$NR_2SO_2R_3$ or —$NR_2COOR_5$, or $R_3$ and $R_4$ may together with N form a 5- to 7-membered heterocyclic group; A is a direct bond, lower alkylene, or lower alkene having from 1 to about 10 carbon atoms; and the pharmaceutically acceptable salts thereof. These compounds are useful as β-adrenergic blocking agents and for the treatment of glaucoma.

35 Claims, No Drawings

ESTERS OF 3-(3-SUBSTITUTED-AMINO-2-HYDROXY-PROPOXY)-4-SUBSTITUTED-1,2,5-THIADIAZOLE DERIVATIVES

BACKGROUND OF THE INVENTION

Compounds in accordance with the present invention are useful as β-adrenergic blocking agents for the treatment or prophylaxis of cardiac disorders; and for the treatment of glaucoma or lowering of intraocular pressure by topical administration of the compounds to the eye. These compounds have short duration in the systemic circulation, but have good stability in ocular fluid; and thus are particularly useful as glaucoma agents since they have a low potential for producing unwanted systemic side effects.

Glaucoma is a condition of the eye characterized by increased intraocular pressure. Untreated, the condition can eventually lead to irreversible retinal damage and blindness. Conventional therapy for glaucoma has involved topical administration of pilocarpine and/or epinephrine, administered to the eye several times daily.

The use of various β-blocking agents to lower intraocular pressure is well documented. For example, U.S. Pat. No. 4,195,085 to Stone discloses a method for treatment of glaucoma by the optical administration of a β-blocking compound, timolol maleate. U.S. Pat. No. 4,127,674 discloses a method of treating glaucoma with labetalol, a known antagonist of both alpha and beta adrenergic receptors. However, these methods also possess significant drawbacks, in that the absorption of the β-blocking compound into the systemic circulation can cause undesirable side effects. Such side effects result from prolonged β-blocking action on the heart, bronchioles and blood vessels. For example, according to *Physicians' Desk Reference*, Charles E. Baker, Jr., 35th Edition, 1981, p. 1233, adverse reactions to the topical use of timolol maleate can include bronchospasm and heart failure, as well as cardiac conduction defects. Accordingly, there is a need for a method of treatment for glaucoma or for lowering intraocular pressure which is relatively free of unwanted systemic side effects.

The use of β-blocking agents to lower intraocular pressure can also be accompanied by a local anesthetic activity in the eye which can possibly cause damage to the cornea, and most certainly will cause discomfort to the patient with continued use. There is a need for potent compounds effective in lowering intraocular pressure which have little or no local anesthetic activity in the eye.

The present invention also relates to the treatment or prophylaxis of cardiac disorders. More particularly, the invention relates to a novel method of treatment or prophylaxis of cardiac disorders which comprises administration of β-adrenergic blocking compounds and to compounds useful in such method.

The therapeutic and prophylactic uses of compounds which block sympathetic nervous stimulation of β-adrenergic receptors in the heart, lungs, vascular system and other organs are well documented. Typically, such compounds are administered therapeutically to patients suffering from ischemic heart disease or myocardial infarction for the purpose of reducing heart work, i.e., heart rate and contractile force. Reducing heart work reduces oxygen demand, and may also actually increase oxygen supply. Thus reducing heart work can aid in the prevention of further tissue damage and can relieve angina pectoris.

β-adrenergic stimulation may also aggravate or cause arrhythmias because of increased levels of catecholamines. Thus β-blocking agents may be employed to reduce the risks of arrhythmias.

Heretofore, the emphasis in β-blocker research has been to develop compounds which can be administered to cardiac patients over long periods of time. However, it is often desirable in the critical care setting to quickly reduce heart work or improve rhythmicity during a cardiac crisis, e.g., during or shortly after a myocardial infarction. Conventional β-blocking agents can be employed for such treatment, but their duration of action may be much longer than desired by the physician. A β-blocking agent possessing a long duration of action does not allow precise control of heart work or prompt reversal of the β-blocking effect, which may be required in a critical care setting. For instance, if heart output becomes dangerously low, it is desirable to quickly reduce or eliminate β-blocking activity. The lingering activity of available β-blocking agents can be counterproductive and can greatly complicate the therapeutic decisions required of the physician during such critical care of cardiac patients.

Accordingly there is a need for a pharmaceutical preparation and method of treatment, employing a β-adrenergic blocking compound having a short duration of action in the systemic circulation.

SUMMARY OF THE INVENTION

The present invention relates to compounds of the formula

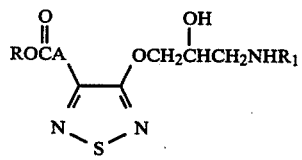

wherein R is lower alkyl, lower cycloalkyl, lower haloalkyl, lower alkylcarboxymethyl, arylcarboxymethyl, lower alkenyl, lower alkynyl, aryl having from 6 to about 10 carbon atoms, or aralkyl; $R_1$ is lower alkyl, lower hydroxyalkyl, lower alkenyl, lower alkynyl, aralkyl, or —WB; where W is alkylene containing from 1 to about 10 carbon atoms; and B is —$NR_2COR_3$, —$NR_2CONR_3R_4$, —$NR_2SO_2R_3$, —$NR_2SO_2NR_3R_4$, or —$NR_2COOR_5$, where $R_2$, $R_3$, $R_4$, and $R_5$ may be the same or different and may be hydrogen, alkyl, alkoxyalkyl, alkoxyaryl, cycloalkyl, alkenyl, alkynyl, aryl, heteroaryl, or aralkyl, except that $R_3$ and $R_5$ are not hydrogen when B is —$NR_2SO_2R_3$ or —$NR_2COOR_5$, or $R_3$ and $R_4$ may together with N form a 5- to 7-membered heterocyclic group; A is a direct bond, lower alkylene, or lower alkene having from 1 to about 10 carbon atoms; and the pharmaceutically acceptable salts thereof.

DETAILED DESCRIPTION OF THE INVENTION

In accordance with the present invention, compounds having the formula

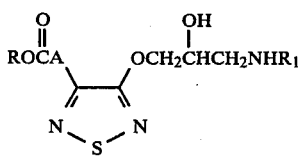

are described, and are shown to have β-adrenergic blocking activity which is particularly useful for the treatment of glaucoma or for lowering intraocular pressure by topical administration to the eye. Compounds in accordance with one embodiment of the present invention are potent β-blockers exhibiting stability in ocular fluid without the unwanted systemic side effects, ocular irritation, and undesirable local anesthetic activities associated with other known β-adrenergic blocking agents.

In accordance with the present invention, R may be a lower alkyl of straight or branched chains having from 1 to about 10 carbon atoms, and preferably from 1 to about 5 carbon atoms such as methyl, ethyl, n-butyl, n-pentyl, and the like; lower cycloalkyl of from 3 to about 7 carbon atoms, and preferably from 3 to about 5 carbon atoms such as cyclopropyl, cyclopentyl, 2-methylcyclopropyl, and the like; lower haloalkyl from 1 to about 10 carbon atoms, and preferably from 1 to about 5 carbon atoms such as halomethyl, haloethyl, halopropyl, and the like where the halogen may be chlorine, bromine, fluorine or iodine illustrated is trifluoromethyl; lower alkylcarboxymethyl in which the alkyl portion contains from 1 to about 5 carbon atoms such as methylene, ethylene, propylene, and the like; arylcarboxymethyl in which the aryl portion contains from 6 to about 10 carbon atoms such as phenyl, indolyl, naphthyl, and the like; lower alkenyl of from 2 to about 5 carbon atoms such as ethenyl, 2-propenyl, 2-methyl-3-butenyl and the like, lower alkynyl of from 3 to about 5 carbon atoms such as propargyl, methylpropargyl and the like; aryl of from 6 to about 10 carbon atoms, or aralkyl wherein the alkyl portion contains from 1 to about 6, and preferably from 1 to about 3 carbon atoms, and the aryl portion represents substituted or unsubstituted monocyclic or polycyclic aromatic or heterocyclic ring systems of from 6 to about 10 carbon atoms such as benzene, napthalene, anthracene, indolyl, fluorenyl, carbostyryl, and carbazolyl. In a most preferred embodiment of the present invention, R is a lower alkyl such as methyl or ethyl.

In accordance with the present invention, A may be a direct bond between the ester and the thiadiazole group; a lower straight or branched chain alkylene of from 1 to about 10 carbon atoms and preferably from 1 to about 5 carbon atoms such as methylene, ethylene, propylene, butylene, 2-methyl-3-butenyl, and the like; or lower straight or branched chain alkene of from 2 to about 10 carbon atoms and preferably from 2 to about 5 carbon atoms such as ethenyl, propenyl, butenyl and the like. In a preferred embodiment of the present invention A is an alkylene having from 1 to 3 carbon atoms, and is preferably 2 carbon atoms such as ethylene.

In accordance with one embodiment of the present invention, $R_1$ may be lower straight or branched alkyl of from 1 to about 10 carbon atoms, and preferably from 1 to about 6 carbon atoms such as methyl, propyl, hexyl, isopropyl, t-butyl and the like; lower straight or branched chain hydroxyalkyl of from 2 to about 10 carbon atoms and preferably from 2 to about 6 carbon atoms such as hydroxyethyl, hydroxy-t-butyl, hydroxyisopropyl and the like; lower alkenyl of from 3 to about 10 carbon atoms, and preferably from 3 to about 6 carbon atoms such as, 2-propenyl, 2-methyl-3-butenyl and the like; lower alkynyl of from 3 to about 10 carbon atoms and preferably from 3 to about 5 carbon atoms such as propargyl, methylpropargyl, dimethylpropargyl and the like; or aralkyl wherein the alkyl portion is straight or branched and contains from 1 to about 5 carbon atoms and the aryl portion contains from 6 to about 10 carbon atoms such as benzyl, phenethyl, 3,4-dimethoxyphenethyl, 1-phenyl-2-dimethylethyl, 1-indole-2-dimethylpropyl and the like. In a preferred embodiment of the present invention, $R_1$ is a lower alkyl having from 1 to about 6 carbon atoms.

Alternatively, $R_1$ may be -WB wherein W represents a straight or branched chain alkylene containing from 1 to about 10 carbon atoms and preferably from 1 to about 6 carbon atoms such as methylene, ethylene, propylene, butylene, 1,1-dimethylethylene, 1,1-diethylethylene and the like; and B represents $-NR_2COR_3$, $-NR_2CONR_3R_4$, $-NR_2SO_2R_3$, $-NR_2SO_2NR_3R_4$, or $-NR_2COOR_5$ wherein $R_2$, $R_3$, $R_4$ and $R_5$ may be the same or different and may be hydrogen, alkyl of from 1 to about 10 carbon atoms and preferably from 1 to about 6 carbon atoms, alkoxyalkyl wherein the alkyl groups may be the same or different and contain from 1 to about 10 carbon atoms and preferably from 1 to about 6 carbon atoms; cycloalkyl of from 3 to about 8 carbon atoms, alkenyl of from 3 to about 10 carbon atoms, alkoxyaryl wherein the alkyl group contains from 1 to about 6 carbon atoms, alkynyl of from 3 to about 10 carbon atoms, aryl which includes substituted or unsubstituted monocyclic or polycyclic aromatic or heterocyclic ring systems of from 6 to about 10 carbon atoms such as phenyl, thiophenyl, imidazole, oxazole, indole, and the like, or aralkyl wherein the alkyl portion contains from 1 to about 5 carbon atoms and the aryl portion represents substituted or unsubstituted monocyclic or polycyclic aromatic or heterocyclic ring systems of from 2 to about 10 carbon atoms such as benzyl, phenethyl, 3,4-dimethoxyphenethyl, 1,1-dimethyl-2-(3-indolyl)ethyl and the like; except that $R_3$ and $R_5$ are not hydrogen when B is $-NR_2SO_2R_3$ or $-NR_2COOR_5$, or $R_3$ and $R_4$ may together with N form a 5- to 7-membered heterocyclic group such as pyrrolidine, piperidine, piperazine, morpholine, or thiomorpholine. Such compounds may be administered as their pharmaceutically acceptable acid addition salts, such as the hydrochloride, sulfate, phosphate, gluconate, maleate, tartrate, oxalate, and the like.

Substituents on the aryls of the present invention are those including but not limited to lower alkyl of from 1 to about 4 carbon atoms, lower alkenyl of from 2 to about 5 carbon atoms, alkoxy of from 1 to about 4 carbon atoms, cyano, halogen, amino, acetamino, nitro, hydroxy, hydroxyalkyl wherein the alkyl group contains from 1 to about 4 carbon atoms, or alkylamino wherein the alkyl group contains from 1 to about 4 carbon atoms.

Compounds in accordance with the present invention exist as two stereoisomers due to the presence of an asymmetric carbon atom. This invention includes either stereoisomeric form, as well as racemic mixtures. Chiral compounds are prepared by classical resolution according to the method described in U.S. Pat. No. 4,076,939; such method is herein incorporated by reference. Alternatively, the chiral compounds can be prepared by an asymmetric synthesis described hereinafter. For compounds in which A, R, and $R_1$ represent alkenyl or alkene, both cis and trans isomers are within the scope of the invention.

When used for the treatment of cardiac disorders, the compounds of the present invention are advantageously administered parenterally, e.g., by intravenous injection and preferably by intravenous infusion. Certain compounds having a longer duration of action may be administered orally. Formulations for intravenous injection preferably include the active compound as a soluble acid addition salt in a properly buffered isotonic solution.

The compounds of the present invention have a relatively short systemic duration of action compared to conventional β-blockers. In vitro studies in human whole blood indicate that the ester functions are subject to rapid enzymatic cleavage, resulting in inactive metabolites. Thus, the β-blocking activity in cardiac therapy can be carefully controlled by regulating dosage size and rate of administration. The time required for substantially complete disappearance of the β-blocking effects of the compounds of the present invention ranges from about 10 minutes to about 1 hour or more. Generally, it is preferred that the recovery is accomplished within about ten to fifteen minutes. A short acting β-blocker can advantageously be infused at a rate sufficient to establish an effective blockade in the mammal, wherein the β-blocking ester compound rapidly converts to inactive metabolites upon in vivo enzymatic cleavage, whereupon the infusion is then terminated to effect substantial recovery from the blocking effects within about one hour. Thus, the method in accordance with one embodiment of the invention provides a very useful therapeutic alternative in the treatment or prophylaxis of cardiac disorders.

The dosage administered to a patient and the duration of infusion will depend upon the patient's needs and the particular compounds employed. For short periods of infusion, e.g., less than about three hours, the duration of effect is thought to be determined by both metabolic effects and distribution phenomena. For relatively long periods of infusion, e.g., greater than about three hours, the duration of effect is thought to depend largely on metabolic effects. Accordingly, although the present methods and compounds are generally useful for short term infusion therapy, certain compounds may be preferred for longer durations of infusion. Dosages of about 0.001 to about 100 mg. per kg. of body weight per hour are generally employed with preferred dosages ranging from about 0.01 to about 10 mg. per kg. of body weight per hour.

When used for the treatment of glaucoma or for lowering of the intraocular pressure, the compounds in accordance with the present invention are advantageously administered topically to the eye in the form of a solution, ointment, or solid insert such as is described in U.S. Pat. No. 4,195,085. Formulations may contain the active compound, preferably in the form of a soluble acid addition salt, in amounts ranging from about 0.01 to about 10% by wt., preferably from about 0.5% to about 5% by wt. Unit dosages of the active compound can range from about 0.001 to about 5.0 mg., preferably from about 0.05 to about 2.0 mg. The dosage administered to a patient will depend upon the patient's needs and the particular compounds employed.

Carriers and diluents used in the preparations of the present invention are preferably non-toxic pharmaceutical organic or inorganic compositions such as water; mixtures of water and water-miscible solvents, such as lower alcohols; mineral oils; petroleum jellies; ethyl cellulose; polyvinylpyrrolidone and other conventional carriers. In addition, the pharmaceutical preparations may also contain additional components such as emulsifying, preserving, wetting and sterilizing agents. These include polyethylene glycols 200, 300, 400 and 600, carbowaxes 1,000; 1,500; 4,000; 6,000 and 10,000, bacteriocidal components such as quaternary ammonium compounds, phenylmercuric salts known to have cold sterilizing properties and which are non-injurious in use, thimerosal, methyl- and propyl-paraben, benzyl alcohol, phenyl ethanol, buffering ingredients such as sodium chloride, sodium borate, sodium acetates, gluconate buffers, and other conventional ingredients such as sorbitan monolaurate, triethanolamine, oleate, polyoxyethylene sorbitan monopalmitylate, dioctyl sodium sulfosuccinate, monothioglycerol, thiosorbitol, ethylenediamine tetracetic acid, and the like. Additionally, suitable ophthalmic vehicles can be used as carrier media for the present purpose including conventional phosphate buffer vehicle systems, isotonic boric acid vehicles, isotonic sodium chloride vehicles, isotonic sodium borate vehicles and the like.

The method of treatment in accordance with one embodiment of the present invention advantageously involves the topical administration of eye drops containing the active compound. Formulations for eye drops preferably include the active compound as a soluble acid addition salt in a properly buffered, sterile, aqueous isotonic solution.

The compounds of the present invention are ester group-containing β-blockers that have a selective, localized, β-blocking effect in the eye after topical administration. Such compounds are thought to be rapidly metabolized by plasma and/or liver esterases into inactive by-products, upon entering the systemic circulation. It has been discovered that these same compounds are relatively stable in ocular fluids, i.e., lacrimal fluids and aqueous humor. Consequently, such compounds are useful for the treatment of glaucoma or for lowering intraocular pressure since they remain stable when topically applied to the eye but rapidly metabolize when subsequently absorbed into the systemic circulation.

Some of the compounds may break down in the aqueous humor more rapidly than others. Such compounds may advantageously be employed when only a temporary reduction in intraocular pressure is desired, say for diagnostic procedures. Longer-acting compounds may generally be used for effecting longer-term reductions in intraocular pressure, such as is desired when treating chronic glaucoma. Thus, the method of the present invention provides a very useful therapeutic alternative for the treatment of glaucoma or for lowering intraocular pressure.

In accordance with one embodiment of the present invention the rate of hydrolysis of the ester is influenced by the type of amine substituent. By varying the amine substituent it is possible to vary the length of duration of the compound in the body. The presence of the amine substituent also makes the compounds less lipophilic. Compounds that are less lipophilic have a reduced potential to cause central nervous system effects since there is less potential for CNS penetration.

Compounds in accordance with the present invention may be prepared according to one or more of the general schemes set forth below.

Preparation of the epoxide intermediates from readily available starting material is illustrated in Schemes I–V below:

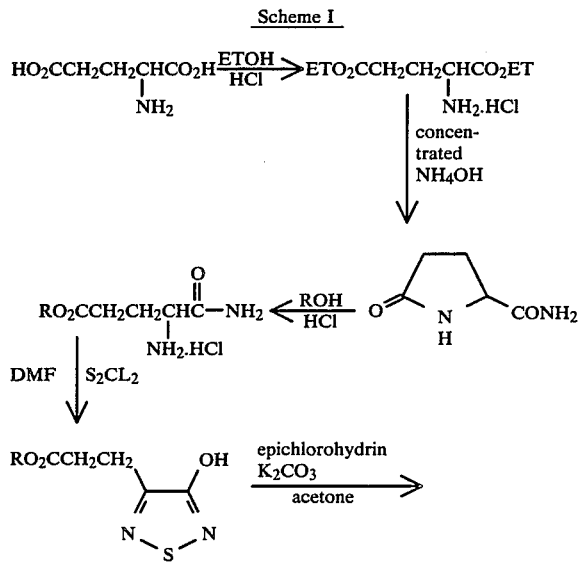

where R is defined as hereinabove, and DMF is dimethylformamide.

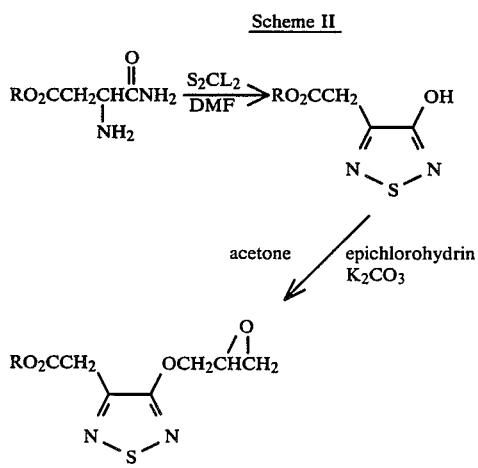

where R is defined as hereinabove and DMF is dimethylformamide. The starting material for this derivative is shown in U.S. Pat. No. 4,076,939 which is herein incorporated by reference.

Scheme III

[Scheme III structures]

were R is defined as hereinabove and n is an integer preferably having from 1 to 10 carbon atoms. The starting material for this derivative is found in U.S. Pat. No. 3,446,813 which is herein incorporated by reference.

Scheme IV
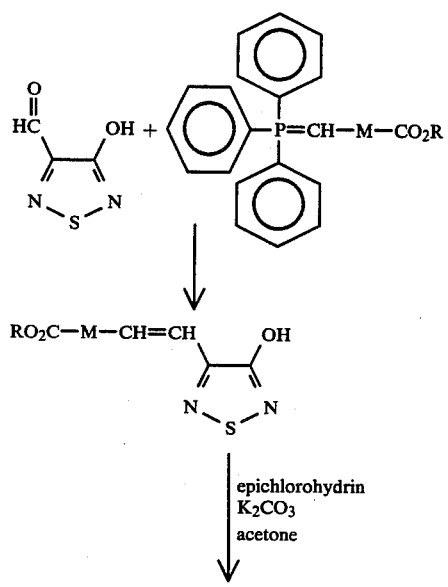
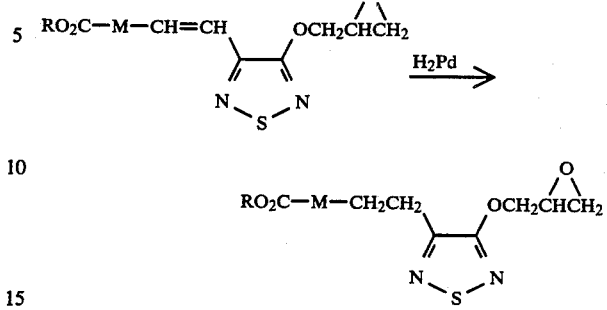
where R is defined as hereinabove; and M is a straight or branched lower alkylene having from 0 to about 10 carbon atoms, wherein the alkene may be at any position within the main chain or branched chain. The phosphorane starting material can be prepared by well known methods such as those described in *Organic Reactions,* Volume 14, Chapter 3, Ed. R. Adams, Wiley, 1965.
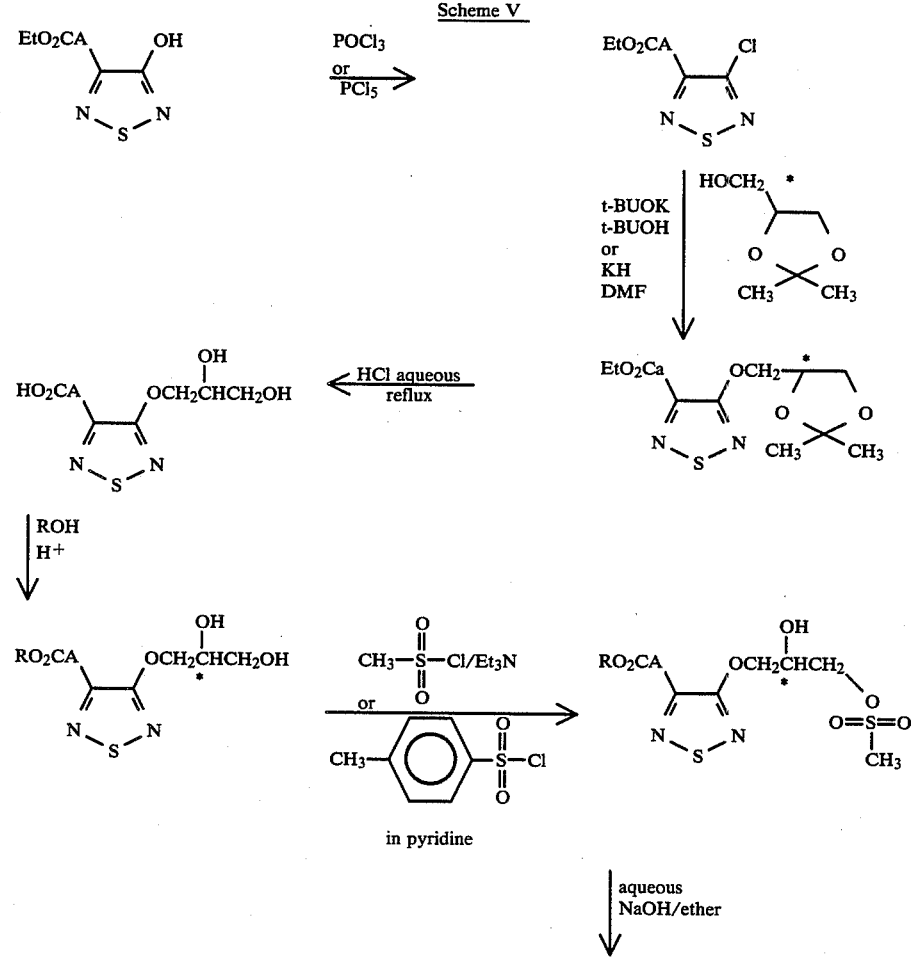

Scheme V -continued

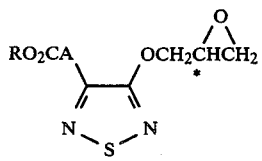

\*R or S configurations

Preparation of β-adrenergic blocking compounds from the corresponding epoxide derivatives is illustrated below:

Scheme VI

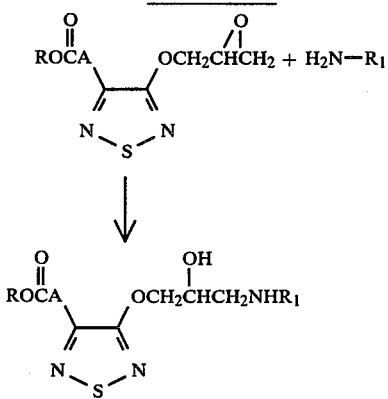

Where R, A, and $R_1$ are defined as hereinabove. This reaction is preferably conducted in an alcoholic solvent identical to the ester adduct to prevent alcoholysis reaction, e.g., when R is methyl, the reaction solvent is preferably methanol.

The compounds in accordance with an alternate embodiment of the present invention may be prepared according to the general scheme below:

Scheme VII

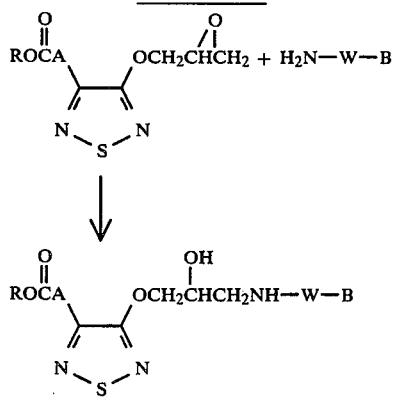

wherein R, A, W and B are defined as hereinabove. This reaction is preferably conducted in an alcoholic solvent identical to the ester adduct to prevent alcoholysis side reactions, e.g., when R is methyl, the reaction solvent is preferably methanol.

Alternatively, the compounds of the present invention, and particularly the compounds wherein B is $-NR_2SO_2NR_3R_4$, may be prepared by reacting the 1,2-epoxy-3-heteroaryloxy-propane with an N-benzyl-protected amine. The protecting group is then conveniently removed by hydrogenolysis over a palladium catalyst to provide the desired compound as shown below:

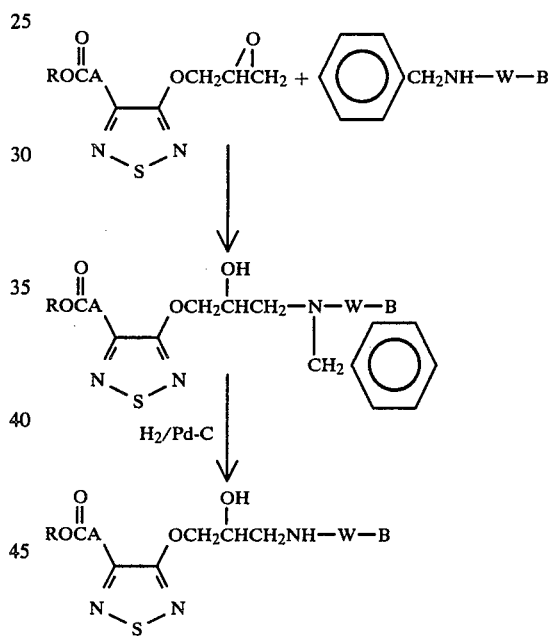

wherein R, W, A, and B are defined as hereinabove.

The amines, $H_2N$-W-B, wherein W and B are defined as hereinbefore may be prepared by specific procedures set forth in the copending patent application Ser. No. 320,772 filed on Nov. 12, 1981. The individual amines and method of preparation are herein incorporated by reference into this application. The general schemes for preparing the amine intermediates are illustrated below:

(a) For amidoalkylamines (B = $NR_2COR_3$)

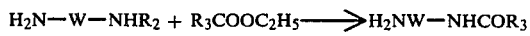

wherein W, $R_2$ and $R_3$ are as defined as hereinabove.
(b) For alkoxycarbonylaminoalkylamines (B = $NR_2COOR_5$), either of two methods may be used:
1.

-continued

2.
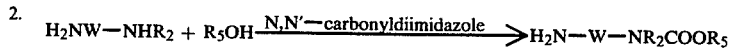

wherein W, R$_2$ and R$_5$ are defined as hereinabove.
(c) For ureidoalkylamines (B = NR$_2$CONR$_3$R$_4$) any of four methods may be used:

(1)
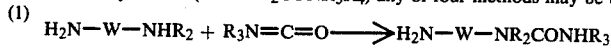

(2)
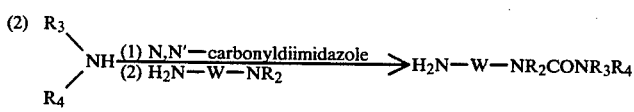

(3)
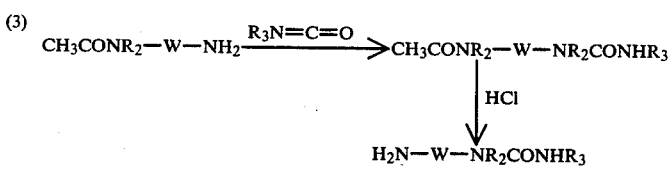

(4)

wherein W, R$_2$, R$_3$ and R$_4$ are defined as hereinabove.
(d) For sulfonamidoalkylamines (B = NR$_2$SO$_2$R$_3$):

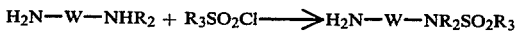

wherein W, R$_2$ and R$_3$ are defined as hereinabove.
(e) For sulfamidoalkylamines (B = NR$_2$SO$_2$NR$_3$R$_4$)

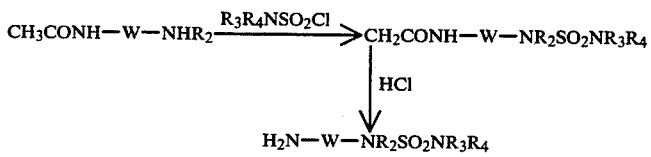

wherein W, R$_2$, R$_3$ and R$_4$ are defined as hereinabove.
(f) Protected N—benzylamine intermediates,

—CH$_2$NH—W—B, may be prepared by the following method:

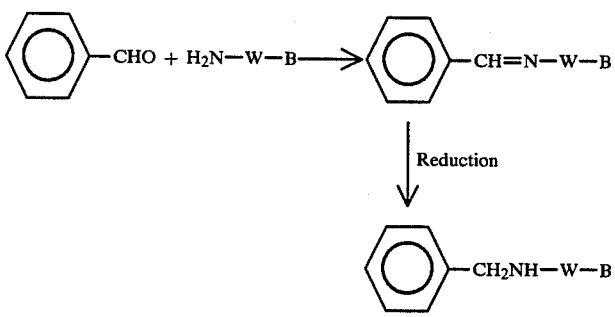

wherein W and B are defined as hereinabove. The reduction may be accomplished by hydrogenation over a catalyst such as palladium-on-carbon or by hydride reagents such as sodium cyanoborohydride.

Compounds embraced by the present invention are those including but not limited to those illustrated below:

Ethyl 3-[3-[2-Hydroxy-3-(isopropylamino)propoxy]-1,2,5-Thiadiazole-4-yl]propionate Ethyl 3-[3-[2-Hydroxy-3-(t-butylamino)propoxy]-1,2,5-Thiadiazole-4-yl]propionate Ethyl 3-[3-[2-Hydroxy-3-(hydroxy-t-butylamino)propoxy]-1,2,5-Thiadiazole-4-yl]propionate Ethyl 3-[3-[2-Hydroxy-3-(1,1,dimethylpropargylamino)propoxy]-1,2,5Thiadiazole-4-yl]propionate Ethyl 3-[3-[2-Hydroxy-3-(benzylamidoethylamino)propoxy]-1,2,5-Thiadiazole-4-yl]propionate Ethyl 3-[3-[2-Hydroxy-3-(indolamidoethylamino)propoxy]-1,2,5-Thiadiazole-4-yl]propionate Ethyl 3-[3-[2-Hydroxy-3-(N-2(acetamidoethyl)amino)propoxy]-1,2,5-Thiadiazole-4-yl]propionate
Ethyl 3-[3-[2-Hydroxy-3-(N-[2-[2-methylpropionamido)ethyl]amino)propoxy]-1,2,5-Thiadiazole-4-yl]propionate
Ethyl 3-[3-[2-Hydroxy-3-(N-[2-(phenylacetamido)ethyl]amino)propoxy]-1,2,5-Thiadiazole-4-yl]propionate
Ethyl 3-[3-[2-Hydroxy-3-(N-2-[N-(phenylaminocarbonyl)amino]ethyl]-amino)propoxy]-1,2,5-Thiadiazole-4-yl]propionate
Ethyl 3-[3-[2-Hydroxy-3-(N-[1,1-dimethyl-2-(aminocarbonylamino)ethyl]amino)propoxy]-1,2,5-Thiadiazole-4-yl]propionate
Ethyl 3-[3-[2-Hydroxy-3-(N-[1,1-dimethyl-2-(1-morpholinocarbonylamino)ethyl]amino)propoxy]-1,2,5-Thiadiazole-4-yl]propionate
Ethyl 3-[3-[2-Hydroxy-3-(N-[2-[N-(4-methylphenylsulfonyl)amino]-ethyl]amino)propoxy]-1,2,5-Thiadiazole-4-yl]propionate
Methyl 3-[3-[2-Hydroxy-3-(isopropylamino)propoxy]-1,2,5-Thiadiazole-4-yl]butyrate
Methyl 3-[3-[2-Hydroxy-3-(t-butylamino)propoxy]-1,2,5-Thiadiazole-4-yl]butyrate
Methyl 3-[3-[2-Hydroxy-3-(hydroxy-t-butylamino)propoxy]-1,2,5-Thiadiazole-4-yl]butyrate
Methyl 3-[3-[2-Hydroxy-3-(benzylamidoethylamino)propoxy]-1,2,5-Thiadiazole-4-yl]butyrate
Methyl 3-[3-[2-Hydroxy-3-(indolamidoethylamino)propoxy]-1,2,5-Thiadiazole-4-yl]butyrate
Methyl 3-[3-[2-Hydroxy-3-(N-2(acetamidoethyl)amino)propoxy]-1,2,5-Thiadiazole-4-yl]butyrate
Methyl 3-[3-[2-Hydroxy-3-(N-[2-[2-methylpropionamido)ethyl]amino)propoxy]-1,2,5-Thiadiazole-4-yl]butyrate
Methyl 3-[3-[2-Hydroxy-3-(N-[2-(phenylacetamido)ethyl]amino)propoxy]-1,2,5-Thiadiazole-4-yl]butyrate
Methyl 3-[3-[2-Hydroxy-3-(N-2-[N-(phenylaminocarbonyl)amino]ethyl]-amino)propoxy]-1,2,5-Thiadiazole-4-yl]butyrate
Methyl 3-[3-[2-Hydroxy-3-(N-[1,1-dimethyl-2-(aminocarbonylamino)ethyl]amino)propoxy]-1,2,5-Thiadiazole-4-yl]butyrate
Methyl 3-[3-[2-Hydroxy-3-(N-[1,1-dimethyl-2-(1-morpholinocarbonylamino)ethyl]amino)propoxy]-1,2,5-Thiadiazole-4-yl]butyrate
Methyl 3-[3-[2-Hydroxy-3-(N-[2-[N-(4-methylphenylsulfonyl)amino]ethyl]amino)propoxy]-1,2,5-Thiadiazole-4-yl]butyrate
Methyl 3-[3-[2-Hydroxy-3-(isopropylamino)propoxy]-1,2,5-Thiadiazole-4-yl]propionate
Methyl 3-[3-[2-Hydroxy-3-(t-butylamino)propoxy]-1,2,5-Thiadiazole-4-yl]propionate
Methyl 3-[3-[2-Hydroxy-3-(hydroxy-t-butylamino)propoxy]-1,2,5-Thiadiazole-4-yl]propionate
Methyl 3-[3-[2-Hydroxy-3-(benzylamidoethylamino)propoxy]-1,2,5-Thiadiazole-4-yl]propionate
Methyl 3-[3-[2-Hydroxy-3-(indolamidoethylamino)propoxy]-1,2,5-Thiadiazole-4-yl]propionate
Methyl 3-[3-[2-Hydroxy-3-(N-2(acetamidoethyl)amino)propoxy]-1,2,5-Thiadiazole-4-yl]propionate
Methyl 3-[3-[2-Hydroxy-3-(N-[2-[2-methylpropionamido)ethyl]amino)propoxy]-1,2,5-Thiadiazole-4-yl]propionate
Methyl 3-[3-[2-Hydroxy-3-(N-[2-(phenylacetamido)ethyl]amino)propoxy]-1,2,5-Thiadiazole-4-yl]propionate
Methyl 3-[3-[2-Hydroxy-3-(N-2-[N-(phenylaminocarbonyl)amino]ethyl]-amino)propoxy]-1,2,5-Thiadiazole-4-yl]propionate
Methyl 3-[3-[2-Hydroxy-3-(N-[1,1-dimethyl-2-(aminocarbonylamino)ethyl]amino)propoxy]-1,2,5-Thiadiazole-4-yl]propionate
Methyl 3-[3-[2-Hydroxy-3-(N-[1,1-dimethyl-2-(1-morpholinocarbonylamino)ethyl]amino)propoxy]-1,2,5-Thiadiazole-4-yl]propionate
Methyl 3-[3-[2-Hydroxy-3-(N-[2-[N-(4-methylphenylsulfonyl)amino]-ethyl]amino)propoxy]-1,2,5-Thiadiazole-4-yl]propionate
Ethyl 3-[3-[2-Hydroxy-3-(isopropylamino)propoxy]-1,2,5-Thiadiazole-4-yl]butyrate
Ethyl 3-[3-[2-Hydroxy-3-(t-butylamino)propoxy]-1,2,5-Thiadiazole-4-yl]butyrate
Ethyl 3-[3-[2-Hydroxy-3-(hydroxy-t-butylamino)propoxy]-1,2,5-Thiadiazole-4-yl]butyrate
Ethyl 3-[3-[2-Hydroxy-3-(benzylamidoethylamino)propoxy]-1,2,5-Thiadiazole-4-yl]butyrate
Ethyl 3-[3-[2-Hydroxy-3-(indolamidoethylamino)propoxy]-1,2,5-Thiadiazole-4-yl]butyrate
Ethyl 3-[3-[2-Hydroxy-3-(N-2(acetamidoethyl)amino)propoxy]-1,2,5-Thiadiazole-4-yl]butyrate
Ethyl 3-[3-[2-Hydroxy-3-(N-[2-[2-methylpropionamido)ethyl]amino)propoxy]-1,2,5-Thiadiazole-4-yl]butyrate
Ethyl 3-[3-[2-Hydroxy-3-(N-[2-(phenylacetamido)ethyl]amino)propoxy]-1,2,5-Thiadiazole-4-yl]butyrate
Ethyl 3-[3-[2-Hydroxy-3-(N-2-[N-(phenylaminocarbonyl)amino]ethyl]-amino)propoxy]-1,2,5-Thiadiazole-4-yl]butyrate
Ethyl 3-[3-[2-Hydroxy-3-(N-[1,1-dimethyl-2-(aminocarbonylamino)ethyl]amino)propoxy]-1,2,5-Thiadiazole-4-yl]butyrate
Ethyl 3-[3-[2-Hydroxy-3-(N-[1,1-dimethyl-2-(1-morpholinocarbonylamino)ethyl]amino)propoxy]-1,2,5-Thiadiazole-4-yl]butyrate
Ethyl 3-[3-[2-Hydroxy-3-(N-[2-[N-(4-methylphenylsulfonyl)amino]-ethyl]amino)propoxy]-1,2,5-Thiadiazole-4-yl]butyrate The in vitro studies hereinafter described indicate that the compounds used in the method of the present invention will undergo different rates of enzymatic hydrolysis depending on their location within the body.

A. Beta Blocking Activity In Vitro

The compounds of the present invention are tested for $\beta$-blocking activity in vitro using guinea pig right atria and guinea pig tracheal strips mounted in a tissue bath containing oxygenated (95% $O_2$-5% $CO_2$) Krebs physiological salt solution at 37° C. Each tissue was suspended between a fixed glass rod and a Statham Universal Transducer connected to a Beckman recorder. Atria were allowed to beat spontaneously under a loading tension of approximately 0.5 gm. Intrinsic depressant or stimulant activity was determined by progressively increasing concentrations in the tissue baths at 60-minute intervals. Tissues were not washed between increments. The maximum concentration showing little or no cardiodepressant activity was chosen for blockage experiments. Changes in rate in response to isoproterenol, a standard $\beta$-receptor agonist, were measured in the absence and presence of test compounds. Spiral strips of guinea pig trachea were suspended under 5 gm resting tension and incubated with phentolamine, tropolone and cocaine. Acttive tension was generated by addition of carbachol $(3.0 \times 10^{-7}M)$ and decreases in tension in response to isoproterenol were quantitated. Cumulative concentration-response curves were produced with isoproterenol both before and after 60-minute incubation of test compounds with atria and trachea. Compounds with β-blocking activity shift concentration-response curves to the right. The blocking potency was estimated by computing $pA_2$ values ($-\log K_B$) by the method of Furchgott, the Pharmacological Differentiation of Adrenergic Receptors, Ann. N.Y. Acad. Sci., 139: 553-570 (1967). Comparison of blockade of right atrial and tracheal responses to isoproterenol permits assessment of cardioselectivity of test compounds; i.e., cardioselective compounds are relatively more effective in blocking atrial rate than tracheal force response to isoproterenol. The degree of cardioselectivity was estimated from the ratio, $K_B$ trachea/$K_B$ atria ($10^{(pA2atria-pA2trachea)}$). A ratio greater than one indicates cardioselectivity. Test drugs are dissolved in distilled water and added to the bath (30 ml) in a volume of 10 or 100 μl.

B. Duration and Potency of Beta-Blocking Action in Vivo

The duration of β-blockade was determined In vivo using pentobarbital-anesthetized dogs instrumented for measurement of heart rate using a Beckman cardiotachometer triggered electronically by a phasic aortic blood pressure signal. Both vagus nerves were severed in the cervical region and the animals were mechanically ventilated. The experimental design used employed a 3-hour infusion of test compound. Bolus doses of isoproterenol (0.5 μg/kg) were used to assess the degree of β-blockade and recovery from β-blockade after determination of the infusion. The doses were spaced at 10-minute intervals and were given before, during and following the infusion of test compounds. The infusion rate was adjusted so that at the end of the 3-hour infusion period the degree of isoproterenol inhibition averaged about 50% of control. Following termination of blocker infusion, percent recovery from β-blockade was computed and the time associated with 80% recovery estimated.

C. Enzymatic Hydrolysis of Beta-Blockers by Dog Blood, Liver Homogenate, and Aqueous Humor Chemicals—Acetonitrile was "HPLC" grade. Distilled water was used to dissolve the compounds and 0.01N HCl was used to dissolve compounds requiring an acidic pH for dissolution.

Enzyme Source—Fresh aqueous humor was collected from eyes of dogs using a 23-gauge needle while fresh dog blood was collected into heparinized Vacutainer tubes. Fresh liver was homogenized in 0.9% NaCl using a Potter-Elvehjem Teflon pestle and glass homogenizer to make a 25% (W/V) homogenate.

Incubation Condition—A 0.5 ml aliquot of dog aqueous humor, blood, or liver homogenate was incubated with 12.5 μg (0.5 ml) of β-blocker in a Dubnoff shaking metabolic incubator at 37° C. for 60 and 120 min. Denatured tissue controls were prepared by adding 2.0 ml of acetonitrile into 0.5 ml of aqueous humor, blood, or liver homogenate to destroy esterase activities prior to addition of the β-blockers. These controls were then incubated at 37° C. for 120 min. After 60 and 120 min, the incubations were terminated by addition of 2 ml of acetonitrile and immediately mixed by a Vortex ® to stop esterase activities.

Sample Processing and Data Analyses—All samples were centrifuged at 4000 RPM for 10 min to sediment denatured proteins. The resultant supernatants were transferred to WISP ® vials and analyzed using an HPLC assay developed for beta blockers. The hydrolysis of β-blockers by aqueous humor, blood, and liver homogenate was determined by disappearance of the compounds. The extent of enzymatic hydrolysis by each tissue was determined by comparing the amount of the compound (absolute peak area) recovered at each time point to the amount of each compound (absolute peak area) in denatured tissue control and aqueous control samples.

D. Half-Lives of Beta Blockers in Dog Whole Blood and Dog Liver Homogenate

The disappearance of the compounds of the present invention in vitro in human whole blood, dog whole blood, and dog liver homogenate is demonstrated by the following assay procedures: the rate of disappearance of a compound is expressed as the half-life (T½), which is the time period in which one half of the initial amount of compound tested disappears. In each experiment, 1 ml of a solution containing 50 μg of the test compound was added to 1 ml of whole blood or 1 ml of a 33% (w/v) liver homogenate. The samples were incubated in a Dubnoff shaking metabolic incubator for 2.5, 5.0, 10.0, 20.0, 30.0 and 60.0 minutes at 37° C. At the designated time periods, the test mixtures were removed from the incubator and transferred to a 0° C. ice bath. Acetonitrile (2 ml) was immediately added and the mixtures were mixed to stop enzymatic hydrolysis. Zero time samples were prepared by adding 2 ml of acetonitrile to denature the proteins prior to addition of the test compounds. After centrifugation to sediment denatured proteins, 2 ml of the supernatant was removed and analyzed by high pressure liquid chromatography, using a mobile phase of 60% acetonitrile/40% 0.05M sodium phosphate buffer (pH 6.6), a U.V. detector and Waters μ Bondapak Phenyl column.

Illustrative of the present invention, an effective β-blocking adrenergic compound was found to have the following unexpected and beneficial pharmacological properties: $pA_2$ (atria), 8.0; $pA_2$ (trachea), 7.4; duration of action, (50% recovery) 10±3 minutes; duration of action, (80% recovery), 22±3 minutes; potency, 7.1±0.03 μg/Kg/minute; T ½ of 10 minutes in dog blood; no significant ocular irritation or local anesthetic activity up to a 30% concentration.

The following examples are provided to illustrate the present invention and are not intended to limit the scope thereof.

EXAMPLE I

Ethyl 3-[3-[2-Hydroxy-3-(t-butylamino)propoxy]-1,2,5-Thiadiazol-4-yl]propionate

This example describes the synthesis of a compound having the formula

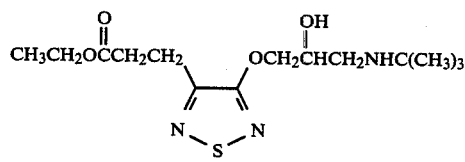

A mixture of 575 g diethyl glutamate and 700 ml concentrated ammonium hydroxide was stirred for 10 hours, and kept in the freezer at (−20° C.) for 5 hours. The resulting white crystalline solid was filtered, washed with 500 ml ethanol followed by 200 ml ether and dried in a vacuum oven at 70° C. for 16 hours to remove the water of crystallization giving 270 g (78.6%) of white crystalline 2-pyrrolidone-5-carboxamide.

A mixture of 135 g 2-pyrrolidone-5-carboxamide and absolute ethanol (USP, dried over 3 Å molecular sieve) containing 1.3 equivalents HCl (prepared by passing HCl gas in 900 g of ethanol until weight=950 grams) was heated under reflux for 45 minutes, filtered while hot to collect ammonium chloride, and washed with ethanol (20 ml). After scratching the inner wall surface and transferring to the freezer (−20° C.) for 2 hours, the white crystalline solid was filtered to give 47.8 g, (24%) of ethyl isoglutaminate.HCl.

To a stirring mixture of sulfur monochloride (2.4 ml) and dry DMF (dried over 4 Å molecular sieve) was added 2.10 g ethyl isoglutaminate hydrochloride as solid over 30 minutes. After stirring was continued for 16 hours, the solution was diluted with 25 ml ice-water and treated with 25 ml ether. The mixture was decanted and the decant was then extracted with ether (4×50 ml), washed with brine (2×50 ml), dried (MgSO4), filtered, treated with charcoal, filtered and evaporated to dryness to give 1.1 g, oil (54.4%) of Ethyl 3-hydroxy-1,2,5-thiadiazole-4-propionate.

A mixture of 1.0 g of Ethyl 3-hydroxy-1,2,5-thiadiazole-4-propionate, 0.68 g anhydrous potassium carbonate, and 1.7 ml epichlorohydrin in dry acetone (dried over 4 Å molecular sieve) was heated under reflux for 16 hours, filtered over celite, evaporated to dryness, kept at 0.2 mm Hg, at 80° C. for 2 hours to eliminate unreacted epichlorohydrin. This epoxide oil was then dissolved in 50 ml CH2Cl2, washed with brine (2×100 ml), dried, (MgSO4) evaporated to dryness giving 1.0 gm (78.4%) of the epoxide derivate.

A mixture of the 1.05 g epoxide derivate prepared above and 1.0 ml t-butylamine (2 equiv.) was refluxed for 10 hours. The reaction mixture was evaporated to dryness, and subjected to high vacuum (0.2 mm) at 65° C. for 2 hours to eliminate excess t-butylamine. The black gummy residue was extracted with ether (3×100 ml), treated with activated charcoal, filtered over celite, and evaporated to a brown residue. This residue was dissolved in 100 ml ethanol and treated with activated charcoal to give a colorless solution after filtration over celite, which was then evaporated to dryness. The residue was dissolved in 10 ml ethylacetate and treated with oxalic acid in ethyl acetate until about pH 2 was obtained. Upon standing overnight, crystalline product was obtained, which was filtered, washed with 50 ml ethylacetate-ether (1:1), recrystallized from ethylacetate-ether to give 800 mg of Ethyl 3-[3-[2-Hydroxy-3-t-butylamino)propoxy]-1,2,5-Thiadiazol-4-yl]propionate mp. 147°–148° C. The IR and NMR spectra were consistent with the assigned structure, and the elemental analysis was consistent with the empirical formula [C14H25N3O4.½(C2H2O4).¼(H2O)].

EXAMPLE II

Ethyl 3-[3-[2-Hydroxy-3-(isopropylamino)propoxy]-1,2,5-Thiadiazole-4-yl]propionate This examples describes the synthesis of a compound having the formula

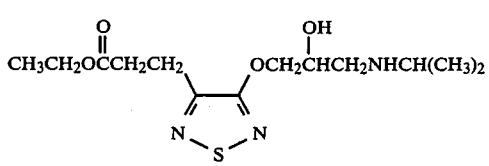

The compound is prepared as in Example I in all essential details with the exception that an equivalent amount of isopropylamine is substituted for t-butylamine.

EXAMPLE III

Ethyl 3-[3-[2-Hydroxy-3-(hydroxy-t-butylamino)propoxy]-1,2,5-Thiadiazole-4-yl]propionate This example describes the synthesis of a compound having the formula

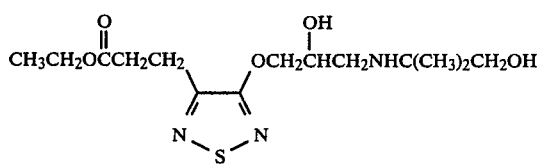

The compound is prepared as in Example I in all essential details with the exception that an equivalent amount of hydroxy-t-butylamine is substituted for t-butylamine.

The present invention has been described in specific detail and with particular reference to its preferred embodiments; however, it will be obvious to those having skill in the art that modifications and changes can be made thereto without departing from the spirit and scope of the invention.

We claim:

1. A compound having the formula

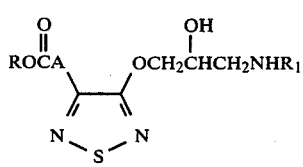

wherein R is lower alkyl, lower cycloalkyl, lower haloalkyl, lower alkyl carboxymethyl, aryl carboxymethyl, lower alkenyl, lower alkynyl, aryl having from 6 to about 10 carbon atoms, or aralkyl; $R_1$ is lower alkyl, lower hydroxyalkyl, lower alkenyl, lower alkynyl, or aralkyl; A is lower alkylene, or lower alkene having from 1 to about 10 carbon atoms; and the pharmaceutically acceptable salts thereof.

2. A compound in accordance with claim 1 wherein R is an alkyl having from 1 to about 10 carbon atoms; $R_1$ is an alkyl having from 1 to about 10 carbon atoms; and A is an alkylene having from 1 to about 5 carbon atoms.

3. A compound in accordance with claim 1 wherein R is an alkyl having from 1 to about 3 carbon atoms; $R_1$ is an alkyl having from 1 to about 6 carbon atoms; and A is alkylene having from 1 to about 3 carbons.

4. A compound in accordance with claim 1 wherein R is an alkyl having from 1 to about 10 carbon atoms, $R_1$ is an alkyl having from 1 to about 10 carbon atoms, and A is ethylene.

5. A compound in accordance with claim 1 wherein R is an alkyl having from 1 to about 3 carbon atoms; $R_1$ is an alkyl having from 1 to about 6 carbon atoms; and A is ethylene.

6. A compound in accordance with claim 5 wherein R is methyl or ethyl.

7. A compound in accordance with claim 1 which is Ethyl 3-[3[2-Hydroxy-3(isopropylamino)propoxy]-1,2,5-Thiadiazol-4-yl]propionate.

8. A compound in accordance with claim 1 which is Ethyl 3-[3[2-Hydroxy-3(tertiary-butylamino)propoxy]-1,2,5-Thiadiazol-4-yl]propionate.

9. A compound in accordance with claim 1 which is Ethyl 3-[3[2-Hydroxy-3(hydroxy-t-butylamino)propoxy]-1,2,5-Thiadiazol-4-yl]propionate.

10. A method for the treatment or prophylaxis of cardiac disorders in a mammal an effective amount of comprising administering to such mammal a shortacting β-blocking compound of the formula

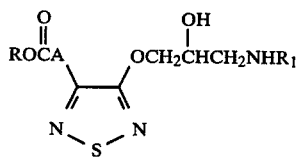

wherein R is lower alkyl, lower cycloalkyl, lower haloalkyl, lower alkyl carboxymethyl, aryl carboxymethyl, lower alkenyl, lower alkynyl, aryl having from 6 to about 10 carbon atoms, or aralkyl; $R_1$ is lower alkyl, lower hydroxyalkyl, lower alkenyl, lower alkynyl, or aralkyl; A is a direct bond, lower alkylene, or lower alkene having from 1 to about 10 carbon atoms; and the pharmaceutically acceptable salts thereof.

11. The method of claim 10 wherein the compound is one in which R is an alkyl having from 1 to about 10 carbon atoms; $R_1$ is an alkyl having from 1 to about 10 carbon atoms; and A is an alkylene having from 1 to about 5 carbon atoms.

12. The method of claim 10 wherein the compound is one in which R is an alkyl having from 1 to about 3 carbon atoms; $R_1$ is an alkyl having from 1 to about 6 carbon atoms; and A is alkylene having from 1 to about 3 carbons.

13. The method of claim 10 wherein the compound is one in which R is an alkyl having from 1 to about 10 carbon atoms, $R_1$ is an alkyl having from 1 to about 10 carbon atoms, and A is ethylene.

14. The method of claim 10 wherein the compound is one in which R is an alkyl having from 1 to about 3 carbon atoms; $R_1$ is an alkyl having from 1 to about 6 carbon atoms; and A is ethylene.

15. The method of claim 14 wherein the compound is one in which R is methyl or ethyl.

16. The method of claim 15 in which the compound is Ethyl 3-[3[2-Hydroxy-3(isopropylamino)propoxy]-1,2,5-thiadiazol-4-yl]propionate.

17. The method of claim 10 in which the compound is Ethyl 3-[3[2-Hydroxy-3-(tertiary-butylamino)propoxy]-1,2,5-Thiadiazol-4-yl]propionate.

18. The method of claim 10 in which the compound is Ethyl 3-[3[2-Hydroxy-3-(hydroxy-t-butylamino)propoxy]-1,2,5-Thiadiazol-4-yl]propionate.

19. A method of treating glaucoma or lowering intraocular pressure in a mammal, which comprises topically applying to the eye of said mammal an intraocular pressure-lowering effective amount of a compound of the formula

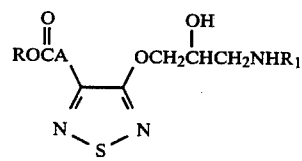

wherein R is lower alkyl, lower cycloalkyl, lower haloalkyl, lower alkyl carboxymethyl, aryl carboxymethyl, lower alkenyl, lower alkynyl, aryl having from 6 to about 10 carbon atoms, or aralkyl; $R_1$ is lower alkyl, lower hydroxyalkyl, lower alkenyl, lower alkynyl, or aralkyl; A is a direct bond, lower alkylene, or lower alkene having from 1 to about 10 carbon atoms; and the pharmaceutically acceptable salts thereof.

20. The method of claim 19 wherein the compound is one in which R is an alkyl having from 1 to about 10 carbon atoms; $R_1$ is an alkyl having from 1 to about 10 carbon atoms; and A is an alkylene having from 1 to about 5 carbon atoms.

21. The method of claim 19 wherein the compound is one in which R is an alkyl having from 1 to about 3 carbon atoms; $R_1$ is an alkyl having from 1 to about 6 carbon atoms; and A is alkylene having from 1 to about 3 carbons.

22. The method of claim 19 wherein the compound is one in which R is an alkyl having from 1 to about 10 carbon atoms, $R_1$ is an alkyl having from 1 to about 10 carbon atoms, and A is ethylene.

23. The method of claim 19 wherein the compound is one in which R is an alkyl having from 1 to about 3 carbon atoms; $R_1$ is an alkyl having from 1 to about 6 carbon atoms; and A is ethylene.

24. The method of claim 23 wherein the compound is one in which R is methyl or ethyl.

25. The method of claim 19 in which the compound is Ethyl 3-[3[2-Hydroxy-3-(isopropylamino)propoxy]-1,2,5-thiadiazol-4-yl]propionate.

26. The method of claim 19 in which the compound is Ethyl 3-[3[2-Hydroxy-3-(tertiary-butylamino)propoxy]-1,2,5-Thiadiazol-4-yl]propionate.

27. The method of claim 19 in which the compound is Ethyl 3-[3[2-Hydroxy-3-(hydroxy-t-butylamino)propoxy]-1,2,5-Thiadiazol-4-yl]propionate.

28. A compound of claim 3 wherein said compound is the d- or l-isomer.

29. A compound of claim 5 wherein said compound is the d- or l-isomer.

30. The compound of claim 7 which is the d-isomer.
31. The compound of claim 7 which is the l-isomer.
32. The compound of claim 8 which is the d-isomer.
33. The compound of claim 8 which is the l-isomer.
34. The compound of claim 9 which is the d-isomer.
35. The compound of claim 9 which is the l-isomer.

* * * * *